United States Patent
Reubens et al.

(10) Patent No.: US 8,476,218 B1
(45) Date of Patent: Jul. 2, 2013

(54) ANTIMICROBIAL COMPOSITIONS AND RELATED METHODS

(75) Inventors: Jay Reubens, Boca Raton, FL (US); David Dyer, Cypress, CA (US)

(73) Assignee: Safehands Solutions, LLC, Westborough, MA (US)

( * ) Notice: Subject to any disclaimer, the term of this patent is extended or adjusted under 35 U.S.C. 154(b) by 0 days.

(21) Appl. No.: 13/442,018

(22) Filed: Apr. 9, 2012

Related U.S. Application Data

(60) Provisional application No. 61/473,358, filed on Apr. 8, 2011.

(51) Int. Cl.
*A01N 25/30* (2006.01)
*A01N 31/10* (2006.01)
*C11D 3/48* (2006.01)

(52) U.S. Cl.
USPC ........... 510/386; 510/131; 510/518; 510/132; 424/400; 424/405

(58) Field of Classification Search
USPC .................. 510/386, 131, 518, 132; 424/400, 424/405
See application file for complete search history.

(56) References Cited

U.S. PATENT DOCUMENTS 6,413,921 B1 * 7/2002 Childers et al. ............... 510/131

* cited by examiner

*Primary Examiner* — Savitha Rao
(74) *Attorney, Agent, or Firm* — Allen, Dyer, Doppelt, Milbrath & Gilchrist, P.A.

(57) ABSTRACT

Antimicrobial compositions and related methods are described. In an embodiment of the invention, an antimicrobial composition comprises parachlorometaxylenol in an amount of 0.75% w/w to 1% w/w; sodium pareth C12-15 sulfonate in an amount of 1% w/w to 1.25% w/w; poly(oxyethylene)20 cetyl ether in an amount of 0.05% w/w to 0.55% w/w; benzoic acid in an amount of 0.075% w/w to 1.25% w/w; glycerol in an amount of 0.01% w/w to 0.02% w/w; phenoxyethanol in an amount of 0.001% w/w to 0.5% w/w; and water in an amount of 94% w/w to 97% w/w.

1 Claim, No Drawings

ANTIMICROBIAL COMPOSITIONS AND RELATED METHODS

CROSS-REFERENCE TO RELATED APPLICATION

Priority is claimed to provisional application Ser. No. 61/473,358 titled "Antimicrobial Compositions and Related Methods," which was filed on Apr. 8, 2011 and is incorporated herein by reference in its entirety.

FIELD OF THE INVENTION

The invention relates to the field of antimicrobial compositions, and, more particularly, to antimicrobial compositions containing parachlorometaxylenol ("PCMX").

BACKGROUND

Illness absenteeism costs companies millions of dollars in lost revenue each year. Employee absenteeism has been called the "last unmanaged cost in business." Journal of Occupational and Environmental Medicine, January 2001, Volume 3. According to a recent survey, "The Total Financial Impact of Employee Absences," Employee Absenteeism, A Guide to Managing Abuse, Anne Coughlin, September 2004, the total cost of absence can equal as much as 36% of payroll when combined with the cost of absence related health care coverage. Of that figure, 9% accounts for unplanned absences. Planned absences, like vacations and holidays, average 26.6%. For a midsize business, illness absenteeism can drain millions of dollars per year from company profits.

Hand washing has been repeatedly demonstrated to reliably limit the spread of microorganisms that cause illness. However, immediate access to soap and water, and the time needed to correctly wash hands are significant barriers to this practice in the workplace, and especially for workers on manufacturing floors. Instant hand sanitizers can be of great use in situations where soap and water are not available for regular hand washing. Several studies have shown that illness absenteeism associated with transmissible pathogens is decreased by 15-50% when rinse free instant hand sanitizers are routinely used (cf. Dyer, et al., 2000; Hammond, et al., 2000, White, et al., 2001 Sandora, 2005). Therefore, using instant hand sanitizers in the workplace can save a Company millions of dollars annually.

The wide variety of instant hand sanitizers available to consumers may be grouped into two categories: alcohol-free and alcohol-containing. Of the former category, quaternary ammonium compounds are most frequently employed as the antimicrobial active chemical entity. Of the latter category, ethanol at a concentration range of 62-70% w/w is most readily available on the market. Both alcohol-free and alcohol-containing products generally are equally effective at reducing germs on the skin with a single use. With repeated use, alcohol-free products show a significant persistence of antimicrobial activity while alcohol-containing products appear to increase the skin's ability to carry disease-causing pathogens.

Microorganisms that spread from human skin can also adversely affect certain aspects of electronics manufacturing processes, and certain of these pose a danger to materials because they can destroy super-hard metal alloys, electric contacts and various polymers. Klintworth, et. al, 1999, reviewed the situation as it applied to electronic instrumentation in space-hardware applications. For example, during previous long-term manned spaceflight missions, more than 100 species of microorganisms were identified on surfaces of materials (bacteria and fungi). Among them were potentially pathogenic ones (saprophytes) capable of active growth on artificial substrates, as well as technophilic bacteria and fungi. Such biotic contaminants can degrade and destroy metals and polymers, resulting in failures and disruptions in the functioning of equipment and hardware. Russian long-term missions SALYUT and MIR have demonstrated that uncontrolled interactions of microorganisms with materials can ultimately lead to the appearance of technological and medical risks, significantly influencing safety and reliability characteristics of individual as well as whole systems and/or subsystems.

On a broader basis of consideration, electronic hardware cleanliness is focused on preventing contaminants. The core IPC standard for cleanliness is IPC-TM-650. IPC-A-610 (mostly section 10.4 for post-solder cleanliness) and J-STD-001 (section 8) derive some of their requirements from that standard. Some chemical contaminants will prevent solder wetting by forming a barrier between flux and the oxides. Others present a physical barrier to the flow of electricity after assembly (grease on gold contacts, for example). Ionic contamination can originate as the vestiges of the acids used to remove oxides, and as other ionic compounds introduced incidentally from workers' hands into circuitry. Examples of chemicals which present a high risk for interfering with electronic circuit function include, but are not limited to, amine or ammonium compounds, silicon and related compounds, and terpenes.

Parachlorometaxylenol ("PCMX") has a phenolic chemical structure and is related to compounds such as cresol, carbolic acid, and hexachlorophene. PCMX is particularly effective against a wide variety of gram-positive and gram-negative bacteria. PCMX goes by a variety of other names, including chloroxylenol; 4-chloro-3,5xylenol; 4-chloro-3,5-dimethylphenol; 2-chloro-m-xylenol; 2-chloro-5-hydroxy-m-xylene; 2-chloro-5-hydroxy-m-xylene; 2-chloro-5-hydroxy-1,3-dimethylbenzene; 4-chlor-1-hydroxy-3,5-dimethyl benzene; and 3,5-dimethyl-4-chlorophenol.

PCMX is desirable for use as an antimicrobial active ingredient in rinse-free hand sanitizer compositions due to the fact that it is unlikely to interfere with electronic circuitry at concentrations resulting from incidental contact from workers' hands. However, PCMX-containing formulations are difficult to prepare due to the incompatibility of PCMX with many surfactants as well as other types of compounds. The efficacy of PCMX is often compromised by a variety of factors, such as additional ingredients (e.g., surfactants), pH level, and solubility.

SUMMARY

In view of the foregoing it is an object of the invention to provide a composition that reduces or eliminates microbes on the skin and also minimizes the potential of contaminating electronics sensitive electronic components. In a preferred embodiment, the composition comprises: parachlorometaxylenol in an amount of 0.75% w/w to 1% w/w; sodium pareth C12-15 sulfonate in an amount of 1% w/w to 1.25% w/w; poly(oxyethylene)20 cetyl ether in an amount of 0.05% w/w to 0.55% w/w; benzoic acid in an amount of 0.075% w/w to 1.25% w/w; glycerol in an amount of 0.01% w/w to 0.02% w/w; phenoxyethanol in an amount of 0.001% w/w to 0.5% w/w; and water in an amount of 94% w/w to 97% w/w.

These and other objects, aspects, and advantages of the present invention will be better appreciated in view of the following detailed description of preferred embodiments.

DETAILED DESCRIPTION PREFERRED EMBODIMENTS

In the Summary above and in the Detailed Description of Preferred Embodiments, reference is made to particular features (including method steps) of the invention. It is to be understood that the disclosure of the invention in this specification includes all possible combinations of such particular features. For example, where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other ingredients, features, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

In this section, the invention will be described more fully with reference to certain preferred embodiments. This invention may, however, be embodied in many different forms and should not be construed as limited to the embodiments set forth herein.

Certain embodiments of the antimicrobial composition are useful as rinse-free instant hand sanitizers for use by the manufacturing workforce in the electronics industry in order to limit the spread of illness absenteeism and to significantly decrease the likelihood of contaminating components resulting from incidental contact. Antimicrobial compositions of the invention preferably do not contain chemical components that will interfere with the assembly or proper function of electronic circuitry and hardware at concentrations anticipated from incidental contact from a worker's hands.

Antimicrobial compositions according to embodiments of the invention comprise a combination of parachlorometaxylenol (PCMX) and other ingredients, including surfactants, co-solvents and emollients which will provide an instant hand sanitizer with significant antimicrobial activity against a broad spectrum of pathogens, including Gram positive and Gram negative bacteria, yeasts, molds fungi and viruses, and that is amenable to frequent use on human hands, and whose excipients are compatible with the chemical constraints of the electronics manufacturing industries. Although the preferred active agent is PCMX, other suitable active agents can be used. These include, but are not limited to, benzalkonium chloride, benzalthonium chloride, triclosan, povidone iodine, organo silane, nano-silver and meso-silver.

The preferred antimicrobial agent, PCMX, is present in the composition at a concentration that is antimicrobially effective, such as about 0.1-3.0% w/w, preferably 0.5%-2.0% w/w, and more preferably 0.75-1.0% w/w. Commercial sources of PCMX are known to those skilled in the art. Commercially available mixtures containing blends of PCMX with chemicals that are not compatible with the chemical constraints of the electronics manufacturing industries are not preferred.

Antimicrobial compositions of the present invention can further comprise a combination of anionic surfactants which facilitate the solubilization of the preferred active agent, and which act to preserve its antimicrobial activity. In certain embodiments, anionic surfactants in the composition can collectively comprise between about 0.50-3.0% w/w, preferably 0.75-2.5% w/w, and more preferably 1.0-2.0% w/w. Suitable anionic surfactant species can include, but are not limited to, sodium salts of n-alkyl sulfates such as sodium dodecyl sufate, ethoxylated alkyl sulfates, and sarcosine surfactant.

The antimicrobial compositions can further comprise a bridging surfactant to facilitate the solubilization of the preferred active agent, and which acts to preserve its antimicrobial activity. Any number of chemical excipients known in the art can accomplish this. However, a preferred bridging surfactant is poly(oxyethylene)20 cetyl ether (commercially available from ICI, Inc. as Brij 58), which on a hydrophilic-lipophilic scale (HLB) of 0-20, on which 20 is very hydrophilic (polar), has a calculated HLB value of 15.7, and which has a critical micelle concentration (CMC) is reported as 0.007 mM to 0.077 mM; (note CMC values vary with the salt concentration and temperature). Preferred concentrations of this surfactant are in a range of 0.01-0.75% w/w, with a more preferred range of 0.05-0.55% w/w, and with an even more preferred range of 0.1-0.5% w/w.

The antimicrobial compositions can also comprise excipients which are used to adjust pH, and which will not contribute to leaving a harmful residue. Suitable excipients include certain of the carboxylic acids. In a preferred embodiment the excipient is benzoic acid and is present in preferred concentration of 0.01-0.5% w/w, a more preferred concentration of 0.05-0.25% w/w, or an even more preferred concentration range of 0.075-1.25% w/w.

Embodiments of the antimicrobial compositions can also or alternatively comprise other excipients which are used to moderate the effect of anionic surfactants on the skin. A variety of suitable chemical entities are known to those skilled in the art. In one particular embodiment, this excipient is glycerol, and is present in a preferred concentration range of about 0.001-0.05% w/w, a more preferred range of 0.005-0.03% w/w or a more preferred range of about 0.01-0.02%.

Additionally, anionic sulfonate surfactants may be employed. For example sodium pareth C12-15 sulfonate may be present in a preferred concentration range of 0.01-2% w/w, a more preferred concentration range of 0.05-1.5% w/w, or an even more preferred concentration range of 1.0-1.25% w/w. The composition of the present invention can also include other ingredients, including, but not limited to, preservatives.

A particular preferred embodiment of the antimicrobial hand sanitizer composition comprises PCMX as the antimicrobial agent, and an anionic surfactant composition comprising a surfactant having a hydrophobic moiety consisting of a linear alkyl group, and a hydrophilic portion having an ethoxy termination, potentially with a sulfonate group, a sarcosine surfactant, and adjuvants to define the pH of the composition. The preferred anionic surfactant is sodium dodecyl sulfate.

In a more particular embodiment, the antimicrobial composition comprises(% w/w): (a) PCMX in an amount of about 1.0-2.0%, (b) sodium dodecyl sulfate in an amount of about 0.5-2.0%, (c) glycerol in an amount of about 0.01-0.05%, (d) polyethylene 20 cetyl ester in an amount of about 0.2-0.5%, (e) isopropanol as a co-solvent in an amount of about 0.6-0.8%, (f) water in an amount of about 94-97%, (g) an appropriate acidifying agent in the amount of about 0.1-0.2%, and (h) phenoxyethanol in an amount of about 0.001-0.5%.

EXAMPLE

Preparation of an Antimicrobial Composition

An antimicrobial composition according to an embodiment of the invention was prepared using the following procedure:

(1) add sodium dodecyl sulfate to distilled, deionized water at 40° C. to a final concentration of 1.0% w/w with mild agitation to dissolve;
(2) add benzoic acid and glycerol to the above solution to a final concentration of 0.1 and 0.02% w/w with mild agitation to disperse;
(3) add poly(oxyethylene)20 cetyl ether to a final concentration of 0.43% w/w to the above solution with mild agitation to dissolve to prepare a first solution;
(4) prepare a second solution of 20% PCMX dissolved in 70% isopropanol/30% diH2O; and
(5) mix the second solution with the first solution until the concentration of the second solution is 1.25% and the mixture is completely clear.

The invention has been described above with reference to preferred embodiments. Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. However, the skilled should understand that the methods and materials used and described are examples and may not be the only ones suitable for use in the invention.

Moreover, it should also be understood that any temperature, weight, volume, time interval, pH, salinity, molarity or molality, range, concentration and any other measurements, quantities or numerical figures expressed herein are intended to be approximate and not an exact or critical figure unless expressly stated to the contrary. In addition, as noted above, materials, methods and examples given are illustrative in nature only and not intended to be limiting.

Accordingly, this invention may be embodied in many different forms and should not be construed as limited to the embodiments set forth herein. Rather, these embodiments are provided so that this disclosure will be thorough, complete, and will fully convey the scope of the invention to those skilled in the art. Therefore, in the specification set forth above there have been disclosed typical preferred embodiments of the invention, and although specific terms are employed, the terms are used in a descriptive sense only and not for purposes of limitation. The invention has been described in some detail, but it will be apparent that various modifications and changes can be made within the spirit and scope of the invention as described in the foregoing specification and in the appended claims.

That which is claimed is:
1. An antimicrobial composition comprising:
parachlorometaxylenol in an amount of 0.75% w/w to 1% w/w;
sodium pareth C12-15 sulfonate in an amount of 1% w/w to 1.25% w/w;
poly(oxyethylene)20 cetyl ether in an amount of 0.05% w/w to 0.55% w/w;
benzoic acid in an amount of 0.075% w/w to 1.25% w/w;
glycerol in an amount of 0.01% w/w to 0.02% w/w;
phenoxyethanol in an amount of 0.001% w/w to 0.5% w/w; and
water in an amount of 94% w/w to 97% w/w.

* * * * *